(12) United States Patent
Yalamanchili

(10) Patent No.: US 8,998,838 B2
(45) Date of Patent: Apr. 7, 2015

(54) ADJUSTABLE VALVE FOR IOP CONTROL WITH REED VALVE

(75) Inventor: Satish Yalamanchili, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 438 days.

(21) Appl. No.: 13/433,557

(22) Filed: Mar. 29, 2012

(65) Prior Publication Data

US 2013/0261530 A1   Oct. 3, 2013

(51) Int. Cl.
*A61F 9/00* (2006.01)
*A61F 9/007* (2006.01)
(Continued)

(52) U.S. Cl.
CPC .......... *A61F 9/00781* (2013.01); *F16K 15/144* (2013.01); *A61F 2210/0076* (2013.01); *A61F 9/0017* (2013.01); *F16K 15/031* (2013.01); *F16K 15/14* (2013.01); *A61F 9/007* (2013.01);
(Continued)

(58) Field of Classification Search
CPC .................. A61F 9/00781; A61F 2009/00891; A61F 2210/0076; A61F 9/0017; A61F 9/007; A61M 2005/14204; A61M 2005/14513; A61M 2027/002; A61M 2202/0014; A61M 2202/04; A61M 2205/3334; A61M 2210/0612; A61M 27/002; A61M 5/142; A61M 5/14276; A61M 5/145; A61M 5/14586; A61M 5/14593; A61M 5/155; A61M 5/168; A61M 5/1456; A61M 5/14566; A61M 5/1452; A61M 5/1454; F16K 1/18; F16K 31/521; F16K 15/16; F16K 15/00; F16K 15/03; F16K 15/031; F16K 15/033; F16K 15/035; F16K 15/036; F16K 15/038; F16K 15/14; F16K 15/141; F16K 15/142; F16K 15/144; F16K 15/145; F16K 15/147; F16K 15/148
USPC .................. 604/8, 9, 10, 890.1, 891.1, 892.1; 623/4.1, 5.11; 205/628
See application file for complete search history.

(56) References Cited

U.S. PATENT DOCUMENTS

| 4,089,329 A | 5/1978 | Couvillon et al. |
| 4,206,762 A | 6/1980 | Cosman |

(Continued)

FOREIGN PATENT DOCUMENTS

| DE | 4438201 | 5/1996 |
| EP | 2427097 | 3/2012 |

(Continued)

OTHER PUBLICATIONS

International Search Report and Written Opinion issued for PCT/US2013/033717 dated Jul. 9, 2013, 6 pgs.
(Continued)

*Primary Examiner* — Adam Marcetich
(74) *Attorney, Agent, or Firm* — Haynes and Boone, LLP

(57) ABSTRACT

A drainage device for implantation in an eye of a patient to treat an ocular condition, that includes an implant body portion comprising of a valve portion. The valve portion may comprise a flexible membrane disposed and arranged in a manner to affect flow of aqueous humor through the implant body portion. The device may also include a reed valve disposed downstream of the flexible membrane. The reed valve may be configured to prevent backflow of aqueous humor toward the membrane and configured to stabilize flow by affecting pressure at the flexible membrane. In one aspect, the reed valve is configured to create backpressure at the membrane that affects the rate of flow at the flexible membrane.

17 Claims, 4 Drawing Sheets

(51) Int. Cl.
  *F16K 15/14* (2006.01)
  *F16K 15/03* (2006.01)
  *F16K 15/16* (2006.01)
  *F16K 15/00* (2006.01)
  *A61F 9/008* (2006.01)

(52) U.S. Cl.
  CPC ............. *F16K 15/16* (2013.01); *F16K 15/00* (2013.01); *F16K 15/03* (2013.01); *A61F 2009/00891* (2013.01)

(56) References Cited

U.S. PATENT DOCUMENTS

| | | | |
|---|---|---|---|
| 4,457,757 A | 7/1984 | Molteno | |
| 4,656,827 A | 4/1987 | Puillet | |
| 4,750,901 A | 6/1988 | Molteno | |
| 4,922,913 A | 5/1990 | Waters et al. | |
| 5,005,577 A | 4/1991 | Frenkel | |
| 5,071,408 A * | 12/1991 | Ahmed | 606/108 |
| 5,178,604 A | 1/1993 | Baerveldt | |
| 5,179,953 A | 1/1993 | Kursar | |
| 5,326,345 A * | 7/1994 | Price, Jr. | 604/9 |
| 5,397,300 A | 3/1995 | Baerveldt | |
| 5,476,445 A | 12/1995 | Baerveldt | |
| 5,558,629 A | 9/1996 | Baerveldt | |
| 5,655,898 A * | 8/1997 | Hashimoto et al. | 417/569 |
| 5,910,110 A | 6/1999 | Bastable | |
| 6,007,511 A | 12/1999 | Prywes | |
| 6,047,698 A * | 4/2000 | Magidson et al. | 128/207.12 |
| 6,447,449 B1 | 9/2002 | Fleischman et al. | |
| 6,453,940 B1 * | 9/2002 | Tipton et al. | 137/493.9 |
| 6,468,283 B1 | 10/2002 | Richter et al. | |
| 6,579,235 B1 | 6/2003 | Abita et al. | |
| 6,589,198 B1 * | 7/2003 | Soltanpour et al. | 604/9 |
| 6,682,500 B2 | 1/2004 | Soltanpour et al. | |
| 6,712,764 B2 | 3/2004 | Jeffries et al. | |
| 6,749,568 B2 | 6/2004 | Fleischman et al. | |
| 6,939,299 B1 | 9/2005 | Petersen et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,354,416 B2 | 4/2008 | Quiroz-Mercado et al. | |
| 7,409,863 B2 | 8/2008 | Bateman et al. | |
| 7,612,328 B2 | 11/2009 | Kaiser | |
| 8,182,435 B2 | 5/2012 | Dacquay et al. | |
| 8,257,295 B2 | 9/2012 | Rickard et al. | |
| 2001/0000527 A1 | 4/2001 | Yaron et al. | |
| 2002/0019607 A1 | 2/2002 | Bui | |
| 2002/0049374 A1 | 4/2002 | Abrea | |
| 2002/0099359 A1 | 7/2002 | Santini, Jr. et al. | |
| 2002/0143284 A1 | 10/2002 | Tu et al. | |
| 2002/0193674 A1 | 12/2002 | Fleischmann et al. | |
| 2003/0078487 A1 | 4/2003 | Jeffries | |
| 2003/0225318 A1 | 12/2003 | Montegrande et al. | |
| 2004/0059248 A1 | 3/2004 | Messner et al. | |
| 2004/0073137 A1 | 4/2004 | Lloyd et al. | |
| 2004/0111050 A1 | 6/2004 | Smedley et al. | |
| 2004/0116794 A1 | 6/2004 | Fink et al. | |
| 2004/0186367 A1 | 9/2004 | Fresco | |
| 2004/0254438 A1 | 12/2004 | Chuck et al. | |
| 2004/0254517 A1 | 12/2004 | Quiroz-Mercado et al. | |
| 2005/0159660 A1 | 7/2005 | Montegrande et al. | |
| 2005/0175494 A1 * | 8/2005 | Shibamoto et al. | 418/160 |
| 2005/0271704 A1 | 12/2005 | Tu et al. | |
| 2005/0273033 A1 | 12/2005 | Grahn et al. | |
| 2006/0131350 A1 | 6/2006 | Schechter et al. | |
| 2007/0019156 A1 | 1/2007 | Fink | |
| 2007/0032757 A1 | 2/2007 | Medow et al. | |
| 2007/0106199 A1 | 5/2007 | Krivoy et al. | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischmann et al. | |
| 2007/0212397 A1 | 9/2007 | Roth | |
| 2008/0015421 A1 | 1/2008 | Penner | |
| 2008/0066815 A1 * | 3/2008 | Anderson | 137/846 |
| 2008/0077127 A1 | 3/2008 | Gao et al. | |
| 2008/0125691 A1 | 5/2008 | Yaron et al. | |
| 2008/0129486 A1 | 6/2008 | Jeckelmann et al. | |
| 2008/0228127 A1 | 9/2008 | Burns et al. | |
| 2009/0069648 A1 | 3/2009 | Irazoqui et al. | |
| 2009/0076367 A1 | 3/2009 | Sit et al. | |
| 2009/0143713 A1 | 6/2009 | Van Dam et al. | |
| 2009/0159826 A1 * | 6/2009 | Poulton et al. | 251/157 |
| 2009/0227933 A1 | 9/2009 | Karageozian | |
| 2009/0275924 A1 | 11/2009 | Lattanzio et al. | |
| 2009/0277206 A1 * | 11/2009 | Laufenberg et al. | 62/285 |
| 2009/0312742 A1 | 12/2009 | Pang et al. | |
| 2010/0010416 A1 | 1/2010 | Juan, Jr. et al. | |
| 2010/0042209 A1 * | 2/2010 | Guarnieri | 623/4.1 |
| 2010/0121348 A1 | 5/2010 | Van Der Burg et al. | |
| 2010/0234717 A1 | 9/2010 | Wismer | |
| 2010/0253167 A1 | 10/2010 | Charnley et al. | |
| 2011/0046536 A1 | 2/2011 | Stegmann et al. | |
| 2011/0071454 A1 | 3/2011 | Santos et al. | |
| 2011/0071456 A1 | 3/2011 | Rickard | |
| 2011/0071458 A1 * | 3/2011 | Rickard | 604/9 |
| 2011/0211974 A1 * | 9/2011 | Harper | 417/53 |
| 2011/0248671 A1 | 10/2011 | Santos et al. | |
| 2012/0121449 A1 * | 5/2012 | Borst et al. | 417/559 |
| 2012/0177510 A1 * | 7/2012 | Delong et al. | 417/297 |

FOREIGN PATENT DOCUMENTS

| | | |
|---|---|---|
| WO | WO 93/03665 | 3/1993 |
| WO | WO 98/03665 | 1/1998 |
| WO | WO 99/38470 A2 | 8/1999 |
| WO | WO 99/38470 A3 | 10/1999 |
| WO | WO 01/94784 | 12/2001 |
| WO | WO 03/001991 | 1/2003 |
| WO | WO 03/102632 | 12/2003 |
| WO | WO 2007/127305 A2 | 11/2007 |
| WO | WO 2007/136993 A1 | 11/2007 |
| WO | WO 2008/061043 A2 | 5/2008 |
| WO | WO 2008/084350 | 7/2008 |
| WO | WO 2008/061043 A3 | 9/2008 |
| WO | WO 2009/026499 A1 | 2/2009 |
| WO | WO 2009/049686 A1 | 4/2009 |
| WO | WO 2009/081031 A2 | 7/2009 |
| WO | WO 2009/081031 A3 | 9/2009 |
| WO | WO 2010/093945 | 8/2010 |
| WO | WO 2010/129446 A1 | 11/2010 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |

OTHER PUBLICATIONS

"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine."

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

(56) References Cited

OTHER PUBLICATIONS

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al, "Initial Investigations on Systems for Measuring Intraocular Pressure," Sensors and Actuators, 2000, p. 287-291, vol. 85, Elsevier Science B.V., Germany.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.
International Searching Authority, Search Report and Written Opinion of the International Searching Authority, PCT/US2010/033329, Jul. 13, 2010, 11 pages.
International Searching Authority, Search Report and Written Opinion of the International Searching Authority, PCT/US2010/047600, Dec. 11, 2010, 13 pages.
International Searching Authority, Search Report and Written Opinion of the International Searching Authority, PCT/US2010/047429, Nov. 1, 2010, 11 pages.
International Searching Authority, Search Report and Written Opinion of the International Searching Authority, PCT/US2010/049424, Nov. 26, 2010, 11 pages.
International Searching Authority, Search Report of the International Searching Authority, PCT/US2011/036742, Aug. 17, 2011, 2 pages.
Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.
Neagu Cristina R.; "A Medical Microactuator Based on an Electrochemical Principle"; Thesis at the Twente University,the Netherlands, Enschede; Aug. 28, 1998; pp. 1-162.
Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.
Erik Stemme and Goran Stemme; "A Valveless Diffuser/Nozzle-Based Fluid Pump"; ScienceDirect; Sensors and Actuators A, 39 (1993); pp. 159-167.
International Searching Authority, Written Opinion of the International Searching Authority, PCT/US2010/047605, Dec. 16, 2010, 9 pages.
International Searching Authority, International Search Report of the International Searching Authority, PCT/US2010/047612, Dec. 21, 2010, 7 pages.
International Searching Authority, Written Opinion of the International Searching Authority, PCT/US2010/047612, Dec. 21, 2010, 10 pages.
International Preliminary Report on Patentability issued for PCT/US2013/033717 dated Oct. 9, 2014, 10 pgs.

\* cited by examiner

ADJUSTABLE VALVE FOR IOP CONTROL WITH REED VALVE

BACKGROUND

The present disclosure relates generally to ocular implants for IOP control that use a reed valve to regulate drainage.

Glaucoma, a group of eye diseases affecting the retina and optic nerve, is one of the leading causes of blindness worldwide. Most forms of glaucoma result when the intraocular pressure (TOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 10, cornea 20, iris 30, ciliary body 40, trabecular meshwork 50, Schlemm's canal 60, and anterior chamber 70 are pictured. Anatomically, the anterior segment of the eye includes the structures that cause elevated IOP which may lead to glaucoma. Aqueous humor fluid is produced by the ciliary body 40 which lies beneath the iris 30 and adjacent to the lens 10 in the anterior segment of the eye. This aqueous humor washes over the lens 10 and iris 30 and flows to the drainage system located in the angle of the anterior chamber 70. The angle of the anterior chamber 70, which extends circumferentially around the eye, contains structures that allow the aqueous humor to drain. The trabecular meshwork 50 is commonly implicated in glaucoma. The trabecular meshwork 50 extends circumferentially around the anterior chamber 70. The trabecular meshwork 50 seems to act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber 70. The two arrows in the anterior segment of FIG. 1 show the flow of aqueous humor from the ciliary bodies 40, over the lens 10, over the iris 30, through the trabecular meshwork 50, and into Schlemm's canal 60 and its collector channels.

One method of treating glaucoma includes implanting a drainage device in a patient's eye. The drainage device allows fluid to flow from the anterior chamber of the eye to a drainage site, relieving pressure in the eye and thus lowering IOP.

Conventional drainage devices are passive valves that have limited control over flow rates and are designed to drain fluid from the anterior chamber to a drainage location elsewhere in the eye. These devices have only limited control over the flow rates of fluid through the device, and are often most effective when pressure differentials between the anterior chamber and the drainage site are relatively small. When pressure differentials are larger, such as during the periods immediately following implantation, the passive drainage device can be ineffective in controlling flow leading to high frequency oscillatory pressures, and also may allow excessive drainage leading to an excessively quick drop in pressure and in IOP, possibly resulting in hemorrhaging or chamber collapse. What is needed is a system that provides stabilized flow control through the drainage device even in high pressure differential scenarios, such as immediately following surgery.

The system and methods disclosed herein overcome one or more of the deficiencies of the prior art.

SUMMARY

In one exemplary aspect, the present disclosure is directed to a drainage device for implantation in an eye of a patient to treat an ocular condition. The device may include an implant body portion comprising a valve portion. The valve portion may comprise a flexible membrane disposed and arranged in a manner to affect flow of aqueous humor through the implant body portion. The device may also include a reed valve disposed downstream of the flexible membrane. The reed valve may be configured to prevent backflow of aqueous humor toward the membrane and configured to stabilize flow by affecting pressure at the flexible membrane.

In one aspect, the reed valve is configured to create back-pressure at the membrane that affects the rate of flow at the flexible membrane. In another aspect, the reed valve comprises a flexible reed that deflects to increase and decrease a size of a fluid pathway and comprises a hard stop disposed adjacent the flexible reed and that is disposed to limit the range of deflection of the flexible reed into the fluid passageway of the aqueous humor.

In another exemplary aspect, the present disclosure is directed to a drainage device for implantation in an eye of a patient to treat an ocular condition. It may include an implant body portion comprising a flexible membrane disposed and arranged in a manner to affect flow of aqueous humor through the implant body portion, and may include a passage portion disposed downstream from the flexible membrane. A reed valve may be disposed in the passage portion. The reed valve may comprise a flexible reed having a first end and a second end, where the first end is fixed to the passage portion and the second end is displaceable as a cantilever from a first position substantially restricting flow to a second position permitting relatively increased flow. The reed valve may be configured to stabilize flow by creating back-pressure at the flexible membrane.

In one aspect, the reed valve comprises a hard stop disposed adjacent the flexible reed and that is disposed to limit the range of deflection of the flexible reed into the fluid passageway of the aqueous humor.

In yet another exemplary aspect, the present disclosure is directed to a method of treating an ocular condition. The method may include evaluating a patient having an ocular condition, selecting an implantable drainage device portion based on the patient evaluation from a plurality of drainage devices portions, where each of plurality of drainage device portions having a reed valve with a different flow restricting parameter, and implanting the drainage portion in an eye to treat the ocular condition.

In one aspect, the flow restricting parameter comprises at least one of cracking pressures and hard-stop conditions. In another aspect, selecting an implantable drainage device portion based on the patient evaluation comprises selecting a reed valve independent of a flexible membrane valve, and attaching the selected reed valve to the membrane valve. In yet another aspect, selecting an implantable drainage device portion based on the patient evaluation comprises selecting a reed valve and a flexible membrane valve, the reed valve being disposed downstream of the membrane valve.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
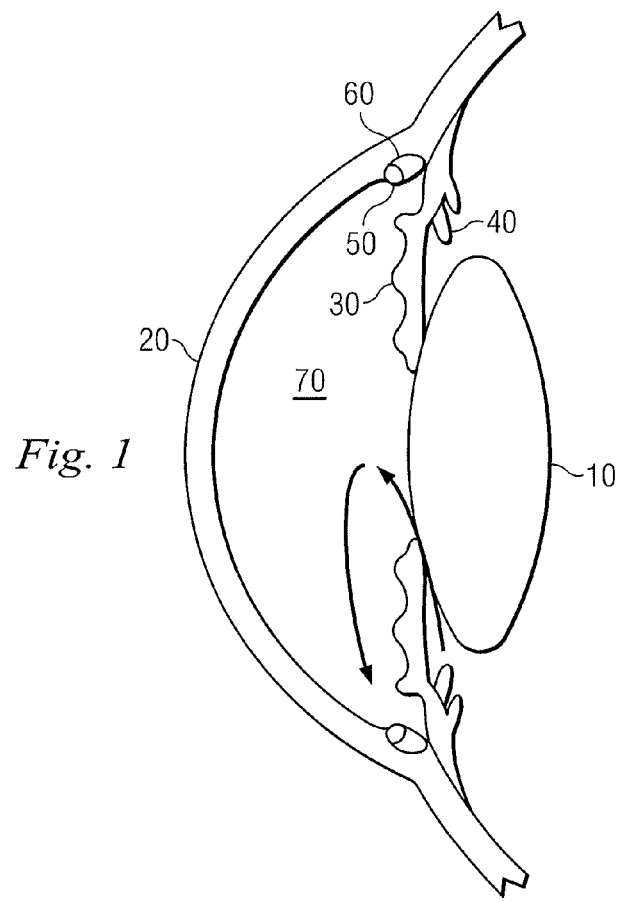
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to a method and system for treating an ocular condition. It relates more specifically to an adjustable flow control valve in series with a reed valve to control the flow rate of aqueous humor through the system in a manner that reduces the occurrence of excessive pressure drops and high frequency oscillatory pressures even during high pressure drop conditions. In turn, this reduces the chance of pressure overshoots resulting in a more stable control of IOP. In one aspect, the reed valve may serve two functions. First, it operates as a check valve to prevent backward flow. Second, unlike conventional check valves such as a ball valve, the reed valve may be designed to provide stabilizing flow control even during higher drop pressure conditions. This is different than conventional spring and ball check valves which have an open condition during higher pressures that permits flow and a closed position at lower pressures that restricts flow. In contrast, the reed valves disclosed herein may stabilize drainage flow during high pressure conditions by maintaining flow at a satisfactory rate while still permitting therapeutic fluid flow at low pressure conditions. This may alleviate the occurrence of high flow pressure drops across the adjustable valve membrane that can occur immediately after implantation of a glaucoma drainage device, resulting in a stable, more controlled drainage from the anterior chamber, resulting in a better patient outcome.

The reed valve opens and closes due to the changing pressure across the surface of the flap. A hard stop can be provided to control the maximum flow through the system. The cracking pressure and the rate of opening are defined by the stress-strain curve of the material of the reed valve used and the net pressure difference across the flap. Sophisticated flaps can be created for different gains at different open positions so as to avoid resonance problems. The range of cracking pressure of the reed valve can be anywhere between 3 mmHg to 100 mmHg.

Figure 2:
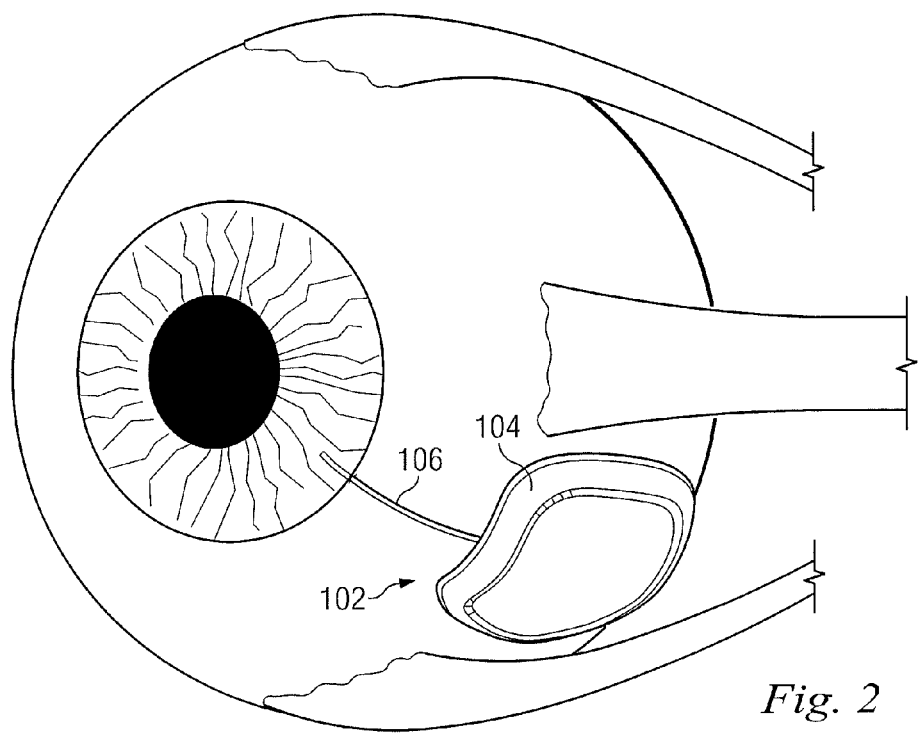
FIG. 2 is an illustration of an exemplary implant disposed in the eye in accordance with one embodiment of the present disclosure.

FIG. 2 shows an exemplary ocular implant 102 disposed on an eye according to one exemplary aspect of the present disclosure. The implant 102 includes a body referred to herein as a plate 104 and a drainage tube 106 that extends from the plate 104. The plate 104 is arranged to carry various components of an IOP control system, and may include a valve, pump, transducers or sensors, a processing system and memory, drug delivery components, a power source or other components that may be used to either control the implant 102 or otherwise treat ocular conditions.

The plate 104 is configured to fit at least partially within the subconjunctival space and is sized for example within a range between about 15 mm×12 mm to about 30 mm×15 mm and has a thickness less than about 2 mm thick and preferably less than about 1 mm thick. The plate 104 may be formed to the radius of the eye globe (about 0.5 inches). It may be rigid and preformed with a curvature suitable to substantially conform to the globe or it may be flexible to conform to the globe. Some embodiments are small enough that conforming to the globe provides little benefit in comfort or implantation technique. The above dimensions are exemplary only, and other sizes and arrangements are contemplated.

When implanted, the plate 104 may be located in the subconjunctival pocket between the conjunctiva and sclera. It may be generally located on an ocular quadrant commonly used for conventional glaucoma drainage devices with plates; that is, it may be centered such that it is equidistant from the neighboring ocular muscles that define the ocular quadrant chosen for implantation. The drainage tube 106 is sized to bridge the anterior chamber and the plate 104 in the subconjunctival pocket to provide an auxiliary flow path for aqueous humor, bypassing the flow-resistive conventional pathway through the trabecular meshwork and shunting aqueous humor directly to a drainage site.

In the example shown, the drainage tube 106 is a single tube having a single lumen. Other embodiments include a plurality of drainage tubes or a plurality of lumens cooperating together to permit fluid to flow through the implant 102. The drainage tube 106 is sized to extend from the plate 104 to the anterior chamber of the eye, as shown in FIG. 2. Aqueous humor may drain through the drainage tube 106 from the anterior chamber to and out of the plate 104 to alleviate elevated intraocular pressure conditions.

Figure 3:
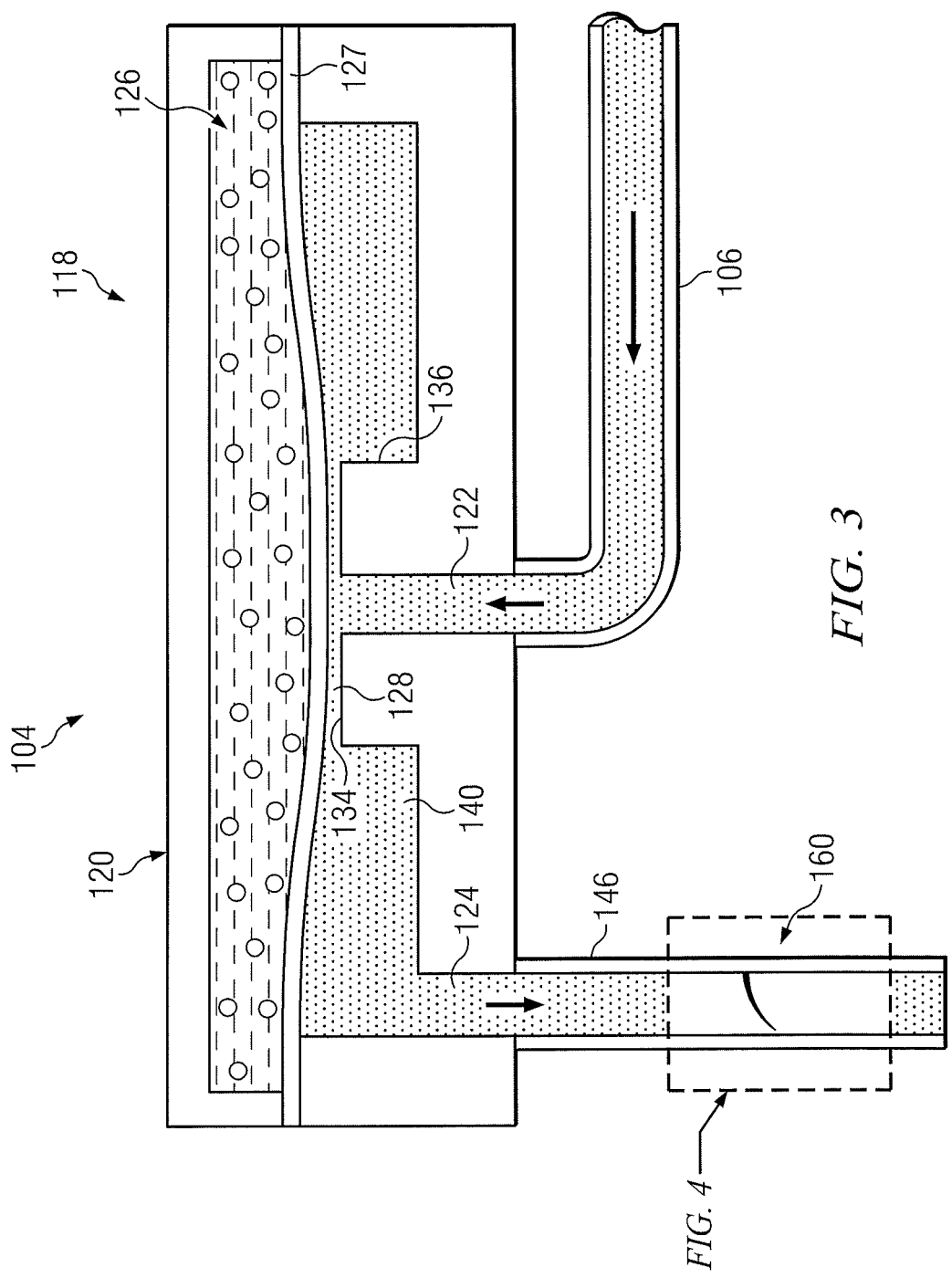
FIG. 3 is a stylized schematic diagram of a cross-sectional view of an exemplary ocular implant according to an exemplary aspect of the present disclosure.

FIG. 3 shows a stylized cross-sectional view of a portion of the plate 104. The plate 104 includes a valve membrane valve system 118 formed of a housing 120 with an entrance port 122 and an exit port 124, a flow control system 126 with a flexible membrane 127 in the housing 120, and a fluid flow passageway 128 extending between the entrance port 122 and the exit port 124. The entrance port 122 connects to the drainage tube 106 and is configured to receive aqueous flowing from the drainage tube 106. The exit port 124 permits fluid to exit the housing 120 for release at a drainage site or for further regulation.

In the example shown, the passageway 128 includes a first portion 134 extending through a boss 136 that is arranged to cooperate with the flow control system 126 to control drainage fluid flow, and a second, larger portion 140 configured in the embodiment shown as a chamber adjacent the boss 136, that less actively impacts the flow through the plate 106. In accordance with this, the first portion 134 of the fluid flow passageway 128 is formed to be substantially perpendicular to the general plane of the flexible membrane 127, and the upper surface of the boss 136 is arranged to be substantially parallel to the general plane of the flexible membrane 127. As such, flow through the first portion 134 is directed in the direction of and directly at the flexible membrane 127. Because of this, the drainage fluid is forced to redirect at an angle of about 90 degrees, although other angles are contemplated. Because of this arrangement, the flexible membrane 127 in this exemplary embodiment can more easily displace only slightly, but still provide a significant modification in the drainage flow. This occurs because the flexible membrane 127 may act in some respects as a cap on the first portion 134 of the fluid flow passageway. In some aspects, the flexible membrane 127 is arranged to cover the entire upper surface of the boss 136, and may even stretch to extend at least partially along the sides of the boss 136 adjacent the edge between the top of the boss 136 and the sides. Accordingly, in such embodiments, the flexible membrane 127 may largely limit or entirely cut off flow through the implant 102.

The second portion 140 of the fluid flow passageway 128 is configured in some respects as a chamber adjacent the boss 136, having a much larger volume. Accordingly, although the second portion 140 of the passageway 128 extends along a portion of the flexible membrane 127, displacement of the membrane does not have as significant an effect on the drainage fluid flow. Accordingly, in this embodiment, the drainage fluid flow is controlled primarily at the region along the top of the boss 136, which in this embodiment is disposed at the central part of the membrane 127.

Some alternative examples the fluid flow passageway 128 include flexible membrane material that may displace to affect fluid flow through the passageway from more than one direction. In some examples, the flexible membrane 127 acts as a toroid or sphincter, with the passageway extending through the hollow center or orifice. In other examples the flexible membrane 127 is disposed on two sides of the passageway. In some of these examples the sides are on opposing sides of the passageway. Some of these embodiments may have two or more separate flexible membranes that cooperate to limit the cross-sectional area of the fluid flow passageway 128.

The flexible membrane 127 may be formed of an elastically deformable elastomeric including without limitation, materials such as a silicone, silicon nitride, silicone elastomeric, polyimide, parylene and others. In the example shown, the flexible membrane is secured to the housing 120 at its edges. In one embodiment, the flexible membrane 127 is a circular material secured at its periphery to the housing 120. In other embodiments, the housing 120 and flexible membrane 127 are formed so that the membrane has a non-circular shape, including oval, substantially rectangular, or square, for example. Other shapes are also contemplated.

In the example in FIG. 3, in addition to the drainage tube 106 extending from the inlet 122 of the plate 104, the ocular implant 102 includes a drainage element 146 that is intended to release fluid to a drainage site after passing through the plate 104 and out of the exit port 124. While shown in FIG. 3 as a drainage tube, the drainage element 146 may be nothing more than the exit port 124 from the implant plate 104 or may be some other drainage passage.

In this embodiment, the drainage element 146 includes a reed valve 160 therein that cooperates to stabilize flow of aqueous humor through the implant 102. The reed valve 160 is disposed downstream of the membrane valve and in this embodiment, serves dual purposes. First, the reed valve 160 operates as a one-way check valve that permits drainage from the anterior chamber, past the membrane valve, and towards the drainage site. Second, the reed valve 160 regulates drainage flow to provide a more stable flow rate for consistent drainage in a manner not achieved by conventional check valves, including ball-type check valves. These advantages will be discussed in greater detail with reference to FIG. 4.

Figure 4:
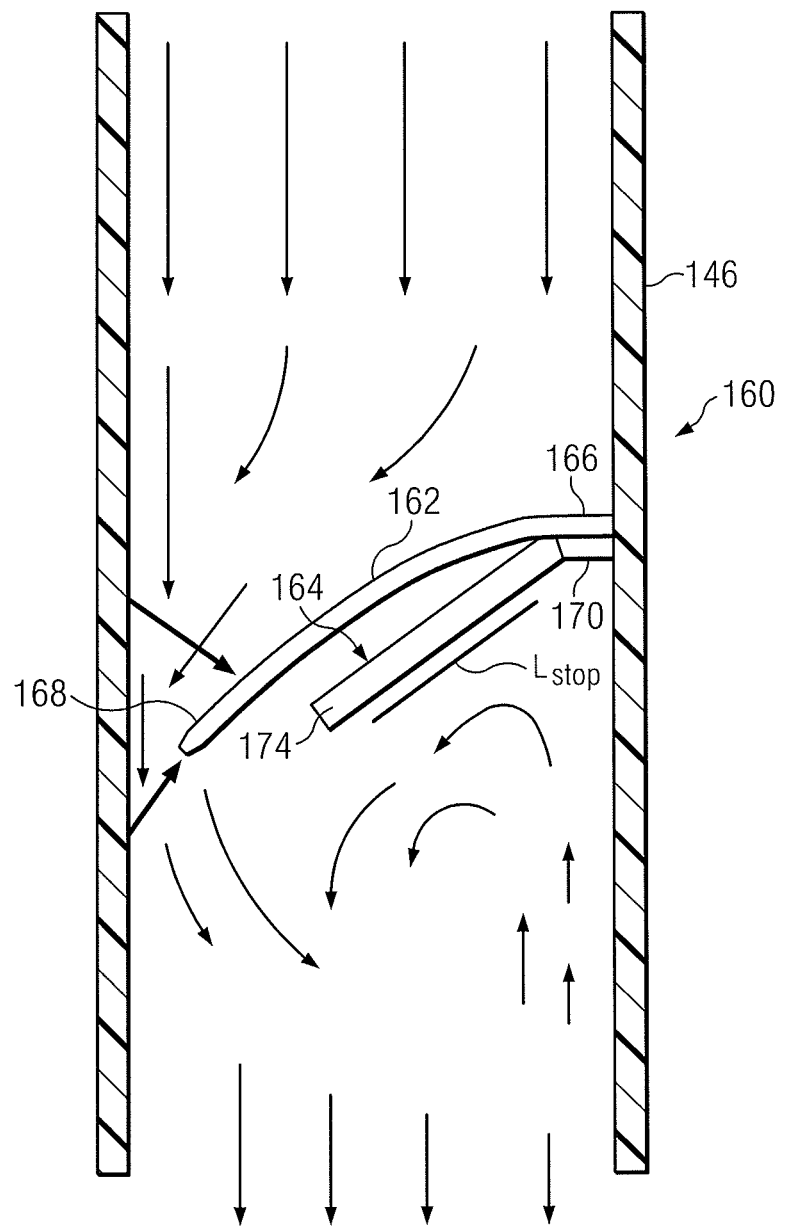
FIG. 4 is a stylized illustration showing an enlarged segment of the ocular implant in FIG. 3 including a reed valve according to an exemplary aspect of the present disclosure.

FIG. 4 is an enlarged portion of FIG. 3 showing the reed valve 160 in greater detail. As can be seen, the drainage valve 146 is a drainage tube, but the drainage element can be an element downstream of the membrane valve 118. For example, it may be a passage within the housing 120 or may be in a flexible tube or other location.

The reed valve 160 in this instance is disposed in the drainage element 146 and comprises a reed 162 and a hard stop 164. The reed 162 includes an attachment end 166 and a cantilevered end 168. The attachment end 166 is fixed in place in the drainage element 146, and the cantilevered end 168 is free to move in one direction away from the wall of the drainage element 146 to allow fluid to pass, and arranged to engage the wall of the drainage element 146 to prevent backflow.

The reed 162 is formed of a flexible material and is configured to deflect, where the amount of deflection is dependent on the pressure of the fluid. The reed 162 deflects based on differentials between upstream pressure, representative of the anterior chamber pressure, and downstream pressure behind the reed valve, representative of pressure at the drainage site. Based on the stiffness, material, and dimensions of the reed 162, the reed valve 160 may have a cracking pressure set at a desired pressure, such as about 3 mmHg. Therefore, when the upstream pressure is greater than the downstream by more than the cracking pressure, the reed valve 160 will begin to open to relieve pressure. In one example, the reed valve is configured and disposed to have a cracking pressure between about 0.25 mmHg and 8 mmHg.

In one example, the reed 162 is formed of a flexible polymer material. In one example, the reed is formed of the same material as the flexible membrane. It may be formed of any suitable material, including, for example without limitation, materials such as a silicone, silicon nitride, silicone elastomeric, polyimide, parylene and others.

In addition, the stiffness, material, and dimensions of the reed 162 can be selected to provide a desired gain in response to pressure. Accordingly, the reed 162 may be selected or designed to deflect a particular amount to permit a particular fluid flow based on the pressure amounts.

In an embodiment, the cross-sectional dimensions or material of the reed 162 changes along the length of the reed. For example, the reed may be controlled to have a flexible distal end portion that deflects during relatively small pressure differentials and a less flexible central portion that deflects in response to relatively higher pressure differential flows. To accomplish this, some exemplary reeds are formed with a tapering body so that the reed has a region of higher stiffness and a region of lower stiffness. Other embodiments include stepped increasing and/or decreasing cross-sections to achieve the desired deflection under the appropriate loads. Some embodiments have substantially uniform thicknesses along the length, as shown in FIG. 4.

The hard stop 164 is disposed downstream of the reed 162 and like the reed, extends from one side of the drainage element 146. The hard stop 164 in this example is a rigid element disposed to limit the range of deflection of the reed 162. In this example it includes a transverse segment 170 extending from a wall of the drainage element 146 and includes an angled segment 174 extending from a distal end of the transverse segment 170. In this embodiment, the transverse segment 170 extends in a direction substantially perpendicular from the wall of the drainage element 146. The transverse segment 170 includes a transverse segment length and the angled segment 174 includes an angled segment length that are selected to provide a desired rigidity and, in cooperation with the membrane 162, to provide a balanced stability during flow conditions. The hard stop 164 is disposed adjacent the reed 162 and is configured to mechanically interfere with the reed deflection to limit the total gain or size of the flow passageway through the reed valve 160. In this example, the hard stop 164 extends more than half the distance across the drainage element.

In one example, the hard stop 164 is disposed to limit the reed deflection to an amount that will limit the flow rate through the valve to prevent overly fast pressure drops in high pressure scenarios. For example, the reed valve 160 may be configured with a deflection resistance that is more controllable than a conventional check valve to prevent excessive gain and thereby stabilize flow during high and low pressure differentials. In one embodiment, the hard stop 164 is located in a manner to affect or limit the deflection of the reed to a particular pressure in the range of 8 mmHg to 15 mmHg. In another embodiment, the hard stop 164 is located in a manner to affect or limit the deflection of the reed when pressures exceed 8 mmHg, 10 mmHg, 12 mmHg, 14 mmHg, or 15 mmHg.

FIG. 4 also shows the fluid flow pattern as a result of the reed valve 160. In this example, the reed valve directs fluid to flow along a side, rather than centrally through the valve. This creates turbulence in the flow downstream of the reed 162. As can be seen, the fluid flow along the wall creates an opposing eddy. Here, the eddy is created substantially on the downstream side of the hard stop 164. Therefore, its effect on the reed 162 is minimized, providing a greater consistency over a variety of differential flow rates and pressure differentials.

Membrane valves in high pressure differential scenarios can flutter, decreasing stability and disrupting smooth or continuous flow from the anterior chamber toward the drainage site. The reed valve 160, with its deflectable reed 162 and the hard stop 164 that limits the displacement of the reed, may stabilize the flow to provide a smooth transition. In addition, because of the control advantages offered by the reed valve 160 over a traditional check valve, such as a ball valve, the reed valve can maintain a backpressure in the system that provides stability in the system during dynamic draining. It does this by creating a backpressure in the system at the membrane valve, thereby controlling flow past the membrane valve. Because of the backpressure, the membrane in the valve is more stable, providing a smoother, more consistent flow. This may provide greater control and flow stability than conventional check valves, such as ball-type check valves.

Figure 5:
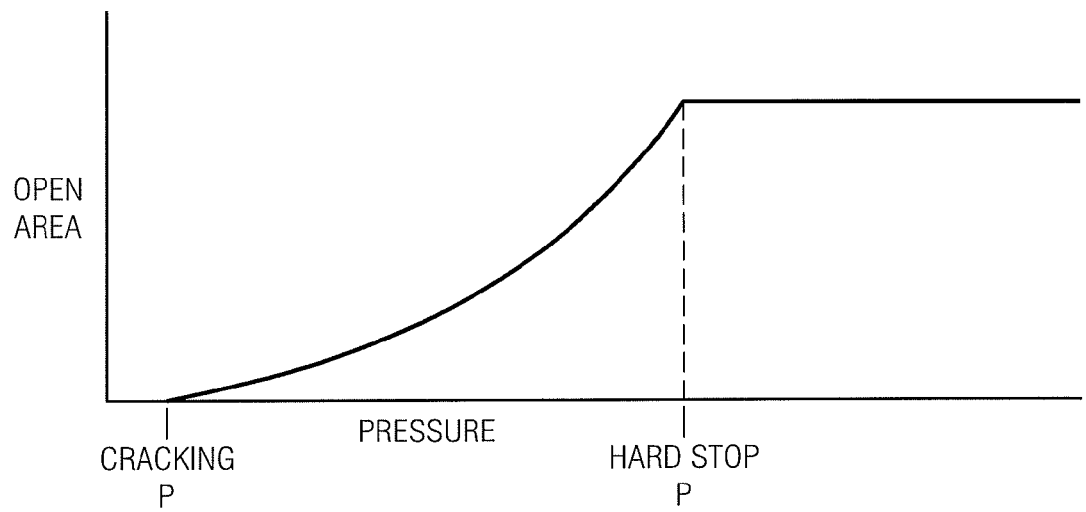
FIG. 5 is a graph showing an exemplary relationship between the amount of open area of the reed valve and pressure at either side of the reed valve.

FIG. 5 shows an exemplary plot displaying the relationship between the gain or cross-sectional area of the reed valve in response to pressure. In FIG. 5, the gain or open area is represented by the y-axis and the fluid pressure through the valve is represented along the x-axis. Starting from the origin, as the pressure increases, at some point, the reed valve will begin to open. This is identified as the cracking pressure on the graph in FIG. 5. In this example, the reed 162 will continue to deflect, and the open area will increase as pressure increases. Here, the curve has a concave shape represented by the exponentially increasing resistance to deflection of the reed 162. As pressure increases, the reed comes into contact with the hard stop 162. Here, the reed valve is prevented from opening further, and even under pressure increases, the gain or open area of the valve may be maintained relatively consistent.

Figure 6:
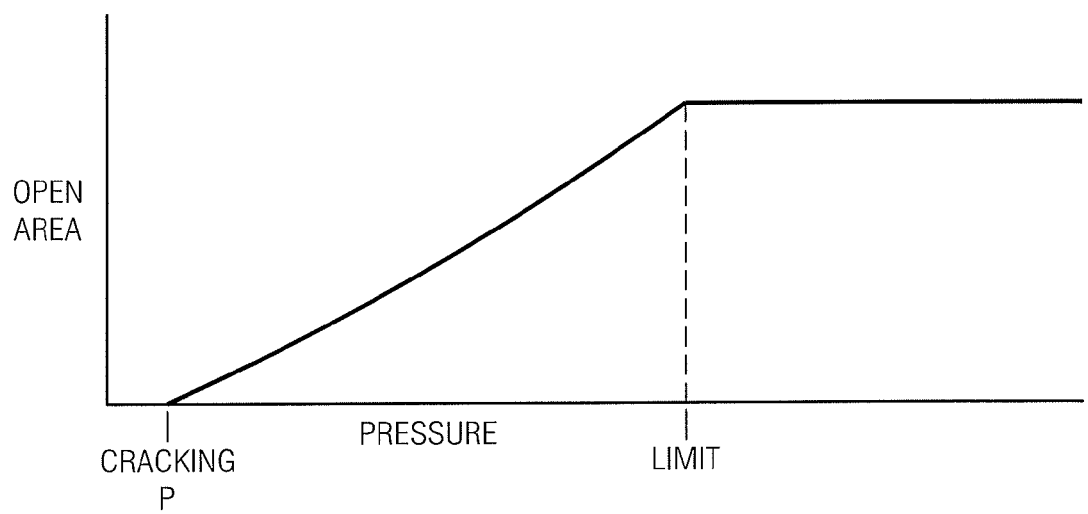
FIG. 6 is a graph showing an exemplary relationship between the amount of open area of a conventional ball-type check valve and pressure acting on the valve.

For comparison, FIG. 6 shows the relationship between the amount of open area of a conventional ball-type check valve and pressure acting on the valve. As can be seen, the conventional ball-type check valve has a consistent or relatively linear change in area as pressure increases. The reed valve has different tendencies than a ball-type check valve because it enables control of the gain, can be used to control flow at low pressure deviations and at higher pressure deviations. The advantage arises because the reed valve can create backpressure that stabilizes flow in even high pressure differential conditions, such as those immediately following surgery. Through the use of the hard stop 164, excessive pressure drops may be reduced, resulting in a more satisfactory implant and better patient outcome.

In one exemplary aspect, the surgeon selects the reed valve 160 to be associated with an implant at the time of implantation to particularly tune the valve to the patient. In this example, the surgeon may be provided with multiple reed valves and may attach the reed valve to the plate 104 depending on patient need. For example, the surgeon may be provided with a plurality of reed valves, where each reed valve differs from each other. For example, one reed valve may be configured to have a cracking pressure of 2 mmHg and may have a hard-stop condition between 8 and 10 mmHg. A different reed valve may have a cracking pressure of 2 mmHg and may have a hard-stop condition between 10 and 12 mmHg. A third reed valve may have a have a cracking pressure of 2 mmHg and may have a hard-stop condition between 12 and 14 mmHg. A different reed valve may have a cracking pressure at 3 mmHg and may have a hard-stop condition between 8 and 10 mmHg. Naturally, the plurality of reed valves could be configured with other ranges and hard stop conditions.

The surgeon may evaluate the patient to determine an expected drainage or flow for the condition or for the patient's physiological condition. He may then select a reed valve that has desired flow restricting parameters. For example, the surgeon may select a reed valve particularly designed to have a particular cracking pressure or a particular pressure limit or hard-stop condition. In one embodiment, the reed valve may then be attached to the plate 106 and implanted in the patient's eye. In another example, the surgeon is provided with multiple fully assembled implants having the reed valve variations discussed above. The surgeon may select the implant that will provide the desired pressure profile.

The reed valve system disclosed herein provides a flow control profile not obtainable with standard ball-type check valves and can be used in high pressure situations to provide stabilizing back pressure that reduces excessive pressure drops to possibly achieve better clinical results while still performing properly during low pressure situations. The reed valve cooperates with the membrane valve to balance the flow through the valve to provide a smooth, controlled drainage without loss of valve control.

In one example, the reed valve is configured to provide a back pressure to the membrane valve that is maintained at a desired level even during pressure variations. This may be designed not only in closed valve situations, such as by the cracking pressure, but also during open conditions, when pressure is flowing.

In one example, an additional ball-type check valve is used downstream of the reed valve. In this example the benefits of stabilizing flow through the membrane may still be obtained while the ball-type check valve may be used to prevent reverse directional flow. In this situation, the back-flow prevention characteristics of the ball-type check valve would be redundant, further decreasing the risk of backflow of fluid from the drainage location to the anterior chamber of the eye.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A drainage device for implantation in an eye of a patient to treat an ocular condition, comprising:
    an implant body portion comprising a valve portion, the valve portion comprising a flexible membrane disposed and arranged in a manner to affect flow of aqueous humor through the implant body portion; and
    a reed valve disposed downstream of the flexible membrane, the reed valve being configured to prevent backflow of aqueous humor toward the membrane and configured to stabilize flow by affecting pressure at the flexible membrane, wherein the reed valve comprises:
    a fluid passageway;
    a flexible reed arranged so that pressure in the fluid passageway acts across substantially an entire length of the flexible reed to crack the reed valve, the flexible reed being deflectable to increase and decrease a size of the fluid passageway; and
    a hard stop disposed adjacent the flexible reed and that is disposed to limit the range of deflection of the flexible reed into the fluid passageway of the aqueous humor.

2. The drainage device of claim 1, wherein the reed valve is configured to create backpressure at the membrane that affects the rate of flow at the flexible membrane.

3. The drainage device of claim 1, wherein the hard stop extends from a wall of the fluid passageway.

4. The drainage device of claim 1, wherein the hard stop includes a first portion extending substantially perpendicular to the direction of flow and a second portion extending downstream from the first portion.

5. The drainage device of claim 1, wherein the hard stop extends more than half the distance across the fluid passageway.

6. The drainage device of claim 1, wherein the reed and the hard stop are balanced to provide a maximum open condition when the IOP is less than 15mmHg.

7. The drainage device of claim 1, wherein the reed valve comprises a reed having a uniform thickness.

8. The drainage device of claim 1, wherein the drainage device comprises a reed having a tapering thickness.

9. The drainage device of claim 1, wherein the reed is configured and disposed to have a cracking pressure between about 0.25mmHg and 8mmHg.

10. The drainage device of claim 1, wherein the hard stop limits deflection of the reed when pressure exceeds at least 8mmHg.

11. The drainage device of claim 1, further comprising a drainage tube extending from the implant body portion and having a distal body configured to extend to and fit within the anterior chamber of the eye.

12. A drainage device for implantation in an eye of a patient to treat an ocular condition, comprising:
    an implant body portion comprising a flexible membrane disposed and arranged in a manner to affect flow of aqueous humor through the implant body portion;
    a passage portion disposed downstream from the flexible membrane; and
    a reed valve disposed in the passage portion, the reed valve comprising a flexible reed having a first end and a second end, the first end being fixed to the passage portion and the second end being displaceable as a cantilever from a first position substantially restricting flow to a second position permitting relatively increased flow, the reed valve being configured to stabilize flow by creating back-pressure at the flexible membrane,
    wherein the reed valve comprises a hard stop disposed adjacent the flexible reed and that is disposed to limit the range of deflection of the flexible reed into passage portion, the hard stop including a first portion extending substantially perpendicular to the direction of flow and a second portion extending downstream from the first portion.

13. The drainage device of claim 12, wherein the hard stop extends from a wall of the passage portion.

14. A drainage device for implantation in an eye of a patient to treat an ocular condition, comprising:
    an implant body portion comprising a valve portion, the valve portion comprising a flexible membrane disposed and arranged in a manner to affect flow of aqueous humor through the implant body portion; and
    a reed valve disposed downstream of the flexible membrane, the reed valve being biased to a closed position that prevents the passage of aqueous humor past the valve, the reed valve having a cracking pressure in the range of about 0.25mmHg and 8mmHg and being configured to prevent backflow of aqueous humor toward the membrane and configured to stabilize flow by affecting pressure at the flexible membrane, wherein the reed valve comprises:
    a flexible reed that deflects to increase and decrease a size of a fluid passageway and has a cross-sectional area that varies along a length of the reed, wherein the flexible reed is a single reed extending across the fluid passageway.

15. The drainage device of claim 14, comprising a hard stop disposed adjacent the flexible reed and that is disposed to limit the range of deflection of the flexible reed into the fluid passageway.

16. The drainage device of claim 14, wherein the hard stop extends from a wall of the fluid passageway.

17. The drainage device of claim 14, wherein the hard stop includes a first portion extending substantially perpendicular to the direction of flow and a second portion angled from the first portion.

* * * * *